United States Patent [19]

Dalcanale et al.

[11] Patent Number: 4,549,025

[45] Date of Patent: Oct. 22, 1985

[54] PROCESS FOR OXIDIZING ALDEHYDES TO CARBOXYLIC ACIDS

[75] Inventors: Enrico Dalcanale; Giorgio Bottaccio, Stefano Campolmi, all of Novara; Fernando Montanari, Milan, all of Italy

[73] Assignee: Montedison S.p.A., Milan, Italy

[21] Appl. No.: 680,825

[22] Filed: Dec. 12, 1984

[30] Foreign Application Priority Data

Dec. 16, 1983 [IT] Italy .............................. 24202 A/83

[51] Int. Cl.⁴ ................. C07C 51/285; C07D 213/807
[52] U.S. Cl. ..................................... 546/327; 549/71; 549/481; 549/484; 562/418; 562/531; 562/533; 562/536
[58] Field of Search ............... 562/418, 531, 533, 536; 546/327; 549/71, 484, 481

[56] References Cited

U.S. PATENT DOCUMENTS 2,443,118  6/1948  Plump ................................. 562/531
3,393,235  7/1968  Boullay ............................... 562/531

FOREIGN PATENT DOCUMENTS 1413926  7/1964  France ................................ 562/531
47-42619 12/1972 Japan ................................. 562/531
48-26738  8/1973  Japan ................................. 562/531
58-46037  3/1983  Japan ................................. 562/531

OTHER PUBLICATIONS

Bal, Tetrahedron, 37 2091–2096, (1981).
Lindgren, Acta, Chem. Scand., 27, pp. 888–890, (1973).

*Primary Examiner*—Michael L. Shippen
*Attorney, Agent, or Firm*—Stevens, Davis, Miller & Mosher

[57] ABSTRACT

Carboxylic acids having the general formula:

R—COOH wherein R is selected from the group consisting of aryl, aralkyl, aralkenyl, aralkynyl, heteroaryl, heteroarylalkyl, heteroarylalkenyl, heteroarylalkynyl, alkyl, alkenyl and alkynyl, optionally substituted by inert or non-reactive substituents under the reaction conditions, are obtained by oxidation of the corresponding aldehydes with an alkali metal or alkaline-earth metal chlorite in the presence of hydrogen peroxide and in an aqueous-organic solvent. The resulting carboxylic acids are utilizable as intermediates for preparing fine chemicals in known ways.

9 Claims, No Drawings

PROCESS FOR OXIDIZING ALDEHYDES TO CARBOXYLIC ACIDS

DESCRIPTION

This invention relates to a process for preparing carboxylic acids from aldehydes.

More particularly, the invention relates to a method of preparing carboxylic acids from aldehydes in the presence of the couple $M(ClO_2)_n/H_2O_2$, where M is an alkali metal or an alkaline-earth metal and n is an integer which may be 1 or 2, at a regulated pH, in aqueous-organic mixed solvents.

The acids obtained correspond to the general formula:

R-COOH    (I)

in which group R is an aryl, aralkyl, aralkenyl, aralkynyl, heteroaryl, heteroarylalkyl, heteroarylalkenyl, heteroarylalkynyl, alkyl, alkenyl or alkynyl, these groups containing up to 20 carbon atoms and being optionally substituted by substituents inert under reaction conditions. Preferred heteroatoms which may be present in group R of Formula (I) are N, O and S.

The carboxylic acids having Formula (I), and obtained according to the process of the present invention, are interesting products usefully employed in a wide range of industrial applications.

In particular, the products defined in Formula (I) are industrially utilized as intermediates for the production of pharmaceutical products (α-aminoacids, etc.), for alimentary uses (synthetic sweeteners, etc.) and, more generally, as intermediates in the field of the so-called fine chemicals.

According to the prior art, the oxidation of aldehydes to carboxylic acids by using chlorites having formula $M(ClO_2)_n$ is carried out in the presence of reagents which are called scavengers and which have the task of subtracting, by forming an addition product therewith, hypochlorous acid HClO which forms as a by-product during the oxidation. In fact, the hypochlorous acid may give rise to undesired secondary reactions, such as addition to double bonds possibly present in the molecule of the aldehyde to be oxidized, epoxidizing reactions, chlorination reactions, etc.

Suitable scavengers known and described, for example, in "Acta Chimica Scandinavica", 27 (1973), 888-890, and in "Tetrahedron", Vol. 37 (1981), 2091-2096, are sulphamic acid, polyphenols and 2-methyl-2-butene. These scavengers form addition compounds with the hypochlorous acid which pollute the desired reaction product, i.e., the carboxylic acid, and are difficult to separate from it.

It is an object of the present invention to provide a process for oxidizing aldehydes to carboxylic acids by means of chlorites, which is characterized by simple operative conditions, high yields of carboxylic acids, and a high purity of such acids.

A still further object of the present invention is that of providing a scavenger of hypochlorous acid which does not give rise to undesired secondary reactions, and which provides byproducts which are removable without difficulties from the reaction product.

It has been found that the above objects, as well as other objects and advantages which will become apparent from the following descrption and examples, are achieved by the process of the present invention, which contemplates the oxidation of aldehydes having the general formula:

R-CHO    (II)

to carboxylic acids R-COOH (I), wherein R is the same as defined above, by using as an oxidant a salt of the type $M(ClO_2)_n$ wherein M and n have the same meanings as defined above and, as a scavenger, hydrogen peroxide, in a mixed aqueous-organic solvent and at a regulated pH ranging from 1 to 6, at a temperature of from 0° to 100° C., according to the following reaction scheme:

$$R-CHO + ClO_2^- \xrightarrow[\text{solvent}]{H^+} R-COOH + HClO$$

In fact, it has been found that hydrogen peroxide, under the reaction conditions employed, acts as a reducing agent towards the hypochlorous acid which has formed during the reaction:

$$HClO + H_2O_2 \rightarrow HCl + H_2O + O_2 \uparrow$$

The products which form in consequence of this reaction are all easily removable from the desired reaction product and do not react with the organic substrate, i.e., with the aldehyde or the carboxylic acid. Furthermore, the use of hydrogen peroxide prevents the formation of chlorine dioxide which results from the reaction between chlorite and hypochlorous acid, which is highly toxic, causing undesired secondary reactions.

The aldehydes utilizable according to the method of the present invention are of the aromatic, araliphatic, heteroaromatic, heteroarylaliphatic and aliphatic types. The aromatic and heteroaromatic nuclei present in the aldehydes may consist of one or more rings, either condensed or not, and contain up to 20 carbon atoms. By way of example only there may be cited: phenyl, naphthyl, diphenyl, furyl, thienyl, pyridyl, etc. The heteroatom may be N, S, O.

The aliphatic groups which are present in the aldehydes may be of the linear or branched type, either saturated or unsaturated, and containing in the aggregate up to 20 carbon atoms: alkyls, alkenyls and alkynyls.

Both the aromatic nuclei and the heteroaromatic nuclei may contain substituents which are inert under the reaction conditions, such as, e.g., halogen-, carboxy-, ester-, ether-, amido-, nitro-, alkyl-, alkenyl-, alkynyl- groups.

The aliphatic groups too may be substituted by substituents inert under the reaction conditions, such as, e.g., halogen-, carboxy-, ester-, ether-, amido-, nitro- groups.

Examples of aldehydes which are oxidizable to the corresponding acids according to the process of the present invention are as follows:

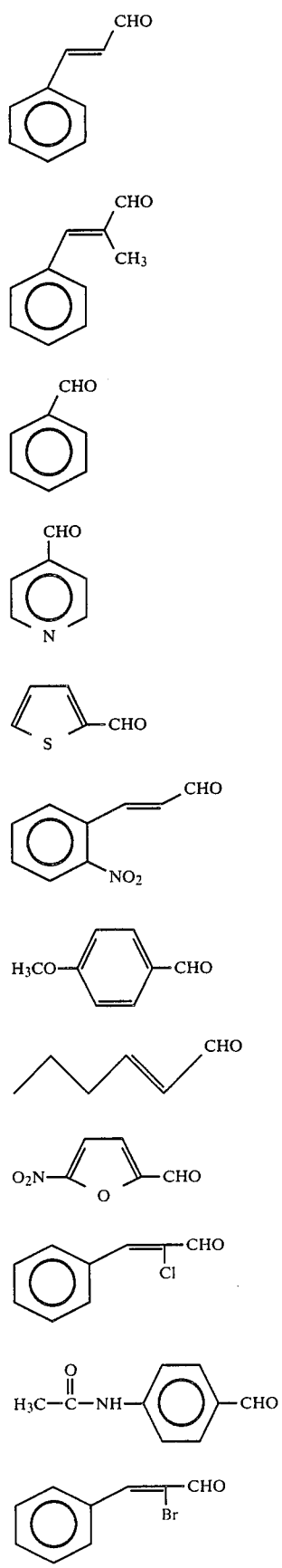

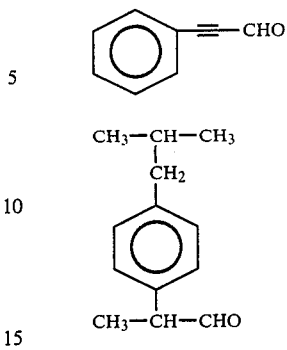

The oxidizing system consists of salts of the type $M(ClO_2)_n$, preferably of sodium and of potassium.

The solvents are composed of water and of organic solvents, either miscible or non-miscible with the aqueous phase. The solvents can belong to the class of the alcohols, of the ethers, either cyclic or not, of the nitriles, etc.

Tetrahydrofuran, acetonitrile, methanol, ethanol, isobutanol, ter.butanol are preferably utilized as solvents.

The temperatures range from 0° to 100° C., and preferably from 10° to 40° C.; the times vary from 2 to 8 hours approximately, and preferably from 2 to 6 hours approximately; the substrate/ $M(ClO_2)_n/H_2O_2$ molar ratios range from 1:1:1 to 1:5:5, and preferably from 1:1:1 to 1:2:5; and the pH is from 1 to 6, and preferably from 3 to 6.

When operating outside the parameters indicated above, the desired oxidation of the aldehyde group to acid either does not occur, or it occurs in an unsatisfactory manner with low selectivities.

The separation of the reaction product is carried out according to conventional techniques.

For example, an extraction is carried out with ether, and the ether extract is extracted, in turn, with aqueous sodium carbonate; the aqueous phase is then acidified and extracted with ether; from the organic phase anhydrified over sodium sulphate and evaporated, the desired product (I) is obtained.

As an alternative, for products insoluble in water, the organic phase of the mixture is evaporated under vacuum, whereupon product (I) precipitates and is separated by filtration.

The remaining aqueous phase is treated with sodium sulphite to remove unreacted residues, if any, of $M(ClO_2)_n$, HClO and $H_2O_2$.

According to one practical embodiment, the process is conducted as follows.

Into a thermoregulated reactor equipped with a magnetic stirrer, a thermometer, a dropping funnel, and a gas outlet connected with a bubbler (bubbling scrubber) there are introduced the solvent, the aldehyde (II), an aqueous solution buffered with monobasic sodium phosphate or other buffer substances usually employed, at a pH equal to about 4.3, and hydrogen peroxide. An aqueous solution of $M(ClO_2)_n$ (III) is dropped in about 2 hours and at room temperature into the reactor containing said mixture. The whole is then allowed to react, always at room temperature, for a predetermined time ranging from 2 to 5 hours until complete disappearance of the aldehyde, which is ascertained by gaschromatography. Product (I) is separated in the manner mentioned before.

Due to the simple operating conditions and to the low cost of the reagents, the process of the present invention is particularly advantageous.

Another advantage consists in the high yields and purity of the products obtained and in the complete conversion of (II), these factors being of particular interest in view of the applications of the products in the field of fine chemicals.

The process will now be still further described in the following examples, which are given however for merely illustrative purposes.

EXAMPLE 1

Into a 250 cc flask, equipped with a magnetic stirrer, a reflux cooler connected with a bubbler, a thermometer and a dropping funnel, there were added in the order:

50 cc of acetonitrile 6.30 cc ($5.0.10^{-2}$ moles) of cinnamaldehyde at 99%, 1.6 g of $NaH_2PO_4$ dissolved in 20 cc of $H_2O$, and 5.00 cc of hydrogen peroxide at 35% ($5.2.10^{-2}$ moles) (oxidimetric titer).

The temperature was maintained at about 30° C. by means of a water bath. To the solution there were added 8.00 g ($7.0.10^{-2}$ moles) of $NaClO_2$ at 79% (iodometric titer) dissolved in 70 cc of $H_2O$.

The addition was carried over a period of time varying from 2 to 4 hours, while the pH varied from 5 to 3.

After the addition, the mixture was allowed to react for 1 hour, and then the product was separated by means of one of the conventional methods, such as extraction with solvent, precipitation, etc.

7.0 g of cinnamic acid were obtained as a crystalline white product, with a yield of 95% calculated on the aldehyde at 99%.

EXAMPLE 2

By operating as in Example 1, but using 50 cc of isobutanol as a solvent and employing 8.00 g ($7.0.10^{-2}$ moles) of $NaClO_2$ at 79% dissolved in 23 cc of $H_2O$. 6.5 g of cinnamic acid were obtained, with a yield of 89% calculated on the aldehyde at 99%.

EXAMPLES 3 TO 5

By operating according to Example 1 and using different solvents, the following results were obtained from the oxidation of cinnamaldehyde to cinnamic acid:

| Example | Solvent | Yield % |
|---|---|---|
| 3 | cc 50<br>$CH_3OH$ | 89% |
| 4 | $CH_3CH_2$—OH | 91% |
| 5 | $H_3C-\underset{\underset{CH_3}{\vert}}{\overset{\overset{CH_3}{\vert}}{C}}-OH$ | 95% |

EXAMPLE 6

By operating as in Example 3, using 25 cc of methanol instead of 50 cc, 6.3 g of cinnamic acid were obtained, with a yield of 86%.

EXAMPLES 7 TO 19

By operating as in Example 1, but using different aromatic, heteroaromatic and aliphatic aldehydes substituted by inert groups, the following results were obtained:

| Example | Aldehyde | Yield % | Solvent |
|---|---|---|---|
| 7 | Ph—CH=C(CH₃)—CHO | 93% | Tetrahydrofuran |
| 8 | Ph—CHO | 93% | $CH_3OH$ |
| 9 |  | 100% | $CH_3CN$ |
| 10 |  | 94% | $CH_3CN$ |
| 11 |  | 98% | $CH_3CN$ |
| 12 |  | 86% | $CH_3CN$ |
| 13 |  | 88% | $CH_3CN$ |
| 14 |  | 84% | $CH_3CN$ (1) |
| 15 | Ph—CH=C(Cl)—CHO | 93% | $CH_3CN$ (2) |
| 16 |  | 96% | $CH_3CN$ + $CH_3OH$ |
| 17 | Ph—CH=C(Br)—CHO | 94% | $CH_3CN$ |
| 18 | Ph—C≡C—CHO | 74% | $CH_3CN$ (1) |
| 19 | p-isobutyl-2-phenylpropionaldehyde | 97% | Isobutanol |

(1) In respect of Example 1, there was used an amount of $H_2O_2$ with a molar ratio to the aldehyde of 5:1 and a pH of about 2.
(2) In respect of Example 1, there was used a higher amount of $NaClO_2$ and of $H_2O_2$: 9.00 g of $NaClO_2$ and 6.00 cc of $H_2O_2$.

EXAMPLE 20 (COMPARATIVE TEST)

Into a 3-neck, 250 cc flask equipped with a magnetic stirrer, a reflux cooler connected with a bubbler, a thermometer and a dropping funnel, there were introduced in the following order:

50 cc of ter.butanol, 6.3 cc of cinnamaldehyde at 99% ($5.10^{-2}$ moles), and 6.3 g of $NH_2SO_3H$ ($6.5.10^{-2}$ moles) in 60 cc of $H_2O$.

In a beaker, a solution containing 7.0 g of $NaClO_2$ at 79% ($6.1.10^{-2}$ moles) in 40 cc of $H_2O$ was prepared; this solution was slowly dropped into the reaction flask over a period of 1 hour. After the addition, the mixture was allowed to react for about 1 hour.

A mixture was thus obtained containing 4.4 g of cinnamic acid, corresponding to a 60% yield calculated on the 99% aldehyde, 1.64 g of cinnamonitrile (by-product obtained in the presence of the scavenger), and 0.1 g of ter.butyl cinnamate.

What is claimed is:

1. A process for oxidizing aromatic, heteroaromatic and aliphatic aldehydes having the general formula:

R-CHO wherein R is selected from the class consisting of aryl, aralkyl, aralkenyl, aralkynyl, heteroaryl, heteroarylalkyl, heteroarylalkenyl, heteroarylalkynyl, alkyl, alkenyl, and alkynyl, optionally substituted by substituents which are inert under the reaction conditions, to the corresponding acids of the general formula:

R-COOH wherein R is the same as defined above, by means of an alkali metal or alkaline-earth metal chlorite, in an aqueous-organic medium, characterized in that it is conducted in the presence of hydrogen peroxide.

2. A process according to claim 1, characterized in that it is conducted at a temperature ranging from 0° to 100° C., and at a pH ranging from 1 to 6.

3. A process according to claim 1, characterized in that the aldehyde/chlorite/hydrogen peroxide molar ratios range from 1:1.1:1 to 1:5:5.

4. A process according to claim 1, characterized in that the chlorite is sodium chlorite or potassium chlorite.

5. A process according to claim 1, characterized in that the reaction medium consists of a mixture of water and of a solvent selected from the class consisting of aliphatic alcohols, cyclic ethers, acyclic ethers, and nitriles.

6. A process according to claim 5, characterized in that the solvent is selected from the class consisting of methanol, ethanol, iso-butanol, ter.butanol, tetrahydrofuran, and acetonitrile.

7. A process according to claim 1, characterized in that the aldehyde R-CHO is selected from the class consisting of cinnamaldehyde, α-methylcinnamaldehyde, benzaldehyde, 4-pyridinaldehyde, 2-thiophenaldehyde, o.nitrocinnamaldehyde, p.methoxybenzaldehyde, 3-propylacrolein, 4-nitro-2-furaldehyde, α-chlorocinnamaldehyde, p.acetamidobenzaldehyde, α-bromocinnamaldehyde, β-phenylpropargylaldehyde, and p-isobutyl-2-phenylpropionaldehyde.

8. A process according to claim 1, characterized in that it is conducted at a temperature ranging from 10° to 40° C., and at a pH ranging from 3 to 6.

9. A process according to claim 1, characterized in that the aldehyde/chlorite/hydrogen peroxide molar ratios range from 1:1.1:1 to 1:2:5.

* * * * *